United States Patent
Du

(10) Patent No.: US 8,388,679 B2
(45) Date of Patent: Mar. 5, 2013

(54) SINGLE CONTINUOUS PIECE PROSTHETIC TUBULAR AORTIC CONDUIT AND METHOD FOR MANUFACTURING THE SAME

(75) Inventor: George Du, Fairfield, NJ (US)

(73) Assignee: Maquet Cardiovascular LLC, Wayne, NJ (US)

( * ) Notice: Subject to any disclaimer, the term of this patent is extended or adjusted under 35 U.S.C. 154(b) by 0 days.

(21) Appl. No.: 12/802,521

(22) Filed: Jun. 8, 2010

(65) Prior Publication Data

US 2011/0112620 A1 May 12, 2011

Related U.S. Application Data

(63) Continuation of application No. 12/387,201, filed on Apr. 29, 2009, now abandoned, which is a continuation of application No. 12/590,906, filed on Nov. 16, 2009, now abandoned, which is a continuation of application No. 11/655,438, filed on Jan. 19, 2007, now abandoned.

(51) Int. Cl.
*A61F 2/06* (2006.01)
(52) U.S. Cl. ......... 623/1.51; 623/1.1; 623/1.5; 623/1.54
(58) Field of Classification Search ............... 623/1.3, 623/1.1, 1.5–1.54
See application file for complete search history.

(56) References Cited

U.S. PATENT DOCUMENTS

| | | | |
|---|---|---|---|
| 1,186,612 A | 6/1916 | Satinover |
| 1,289,015 A | 12/1918 | Suter |
| 2,978,787 A | 4/1961 | Liebig |
| 2,998,030 A | 8/1961 | Koppelman et al. |
| 3,096,560 A | 7/1963 | Liebig |
| 3,316,557 A | 5/1967 | Liebig |
| 3,669,157 A | 6/1972 | Woodall et al. |
| 3,719,212 A | 3/1973 | Emerson et al. |
| 3,805,301 A | 4/1974 | Liebig |
| 3,853,462 A | 12/1974 | Smith |
| 3,945,052 A | 3/1976 | Liebig |
| 3,986,828 A | 10/1976 | Hoffman et al. |
| 4,047,252 A | 9/1977 | Liebig et al. |
| 4,193,137 A | 3/1980 | Heck |
| 4,346,741 A | 8/1982 | Banos et al. |
| 4,443,895 A | 4/1984 | Lane |
| 4,512,761 A | 4/1985 | Raible |

(Continued)

FOREIGN PATENT DOCUMENTS

| | | |
|---|---|---|
| CA | 1131402 A1 | 9/1982 |
| CN | 101610738 A | 12/2009 |

(Continued)

OTHER PUBLICATIONS (Material From Opposition to EP 1 935 375 B2) Anderson, K. Suzanne., "Seamless Textiles with Inherent Shape" North Carolina State University, dated 2004, but not publicly accessible until Jan. 21, 2005, Thesis, cover page and index through p. 228.

(Continued)

*Primary Examiner* — Thomas J Sweet
*Assistant Examiner* — Jason-Dennis Stewart

(57) ABSTRACT

A prosthetic aortic conduit for replacing a root portion of an aorta is provided. The conduit comprises a continuous tubular conduit along a substantially common axis. A portion of the tubular conduit does not substantially deform in a longitudinal direction and has resilient means which allow said another portion of the conduit to be expandable in a lateral direction. The portion that is able to deform laterally mimics the function of the sinuses of Valsalva. The method of manufacturing such a conduit comprises the steps of having a continuous weave of rows of yarn or the equivalent with a change in tightness of the rows so that in some portion of the conduit it is expandable in the lateral direction and in some portion of the conduit it is expandable in the longitudinal direction.

24 Claims, 5 Drawing Sheets

U.S. PATENT DOCUMENTS

| | | | |
|---|---|---|---|
| 4,517,687 A | 5/1985 | Liebig et al. |
| 4,530,113 A | 7/1985 | Matterson |
| 4,567,075 A | 1/1986 | Krawczyk |
| 4,624,822 A | 11/1986 | Arru et al. |
| 4,695,280 A | 9/1987 | Watanabe et al. |
| 4,706,670 A | 11/1987 | Andersen et al. |
| 4,743,250 A | 5/1988 | Kitagawa et al. |
| 4,771,518 A | 9/1988 | LaPointe et al. |
| 4,816,028 A | 3/1989 | Kapadia et al. |
| 4,839,215 A | 6/1989 | Starling et al. |
| 4,842,575 A | 6/1989 | Hoffman et al. |
| 4,867,173 A | 9/1989 | Leoni |
| 4,892,539 A | 1/1990 | Koch |
| 4,969,896 A | 11/1990 | Shors |
| 4,994,072 A | 2/1991 | Bhate et al. |
| 5,070,914 A | 12/1991 | Fukuta et al. |
| 5,108,424 A | 4/1992 | Hoffman et al. |
| 5,121,751 A | 6/1992 | Panalletta |
| 5,127,919 A | 7/1992 | Ibrahim et al. |
| 5,139,515 A | 8/1992 | Robicsek |
| 5,147,400 A | 9/1992 | Kaplan et al. |
| 5,156,619 A | 10/1992 | Ehrenfeld |
| 5,178,630 A | 1/1993 | Schmitt |
| 5,178,634 A | 1/1993 | Ramos Martinez |
| 5,192,296 A | 3/1993 | Bhate et al. |
| 5,197,977 A | 3/1993 | Hoffman et al. |
| 5,217,495 A | 6/1993 | Kaplan et al. |
| 5,246,445 A | 9/1993 | Yachia et al. |
| 5,282,846 A | 2/1994 | Schmitt |
| 5,282,847 A | 2/1994 | Trescony et al. |
| 5,282,848 A | 2/1994 | Schmitt |
| 5,314,443 A | 5/1994 | Rudnick |
| 5,314,468 A | 5/1994 | Ramos Martinez |
| 5,320,639 A | 6/1994 | Rudnick |
| 5,370,682 A | 12/1994 | Schmitt |
| 5,383,892 A | 1/1995 | Cardon et al. |
| 5,383,925 A | 1/1995 | Schmitt |
| 5,385,580 A | 1/1995 | Schmitt |
| 5,413,597 A | 5/1995 | Krajicek |
| 5,413,598 A | 5/1995 | Moreland |
| 5,433,909 A | 7/1995 | Martakos et al. |
| 5,445,599 A | 8/1995 | Edenbaum |
| 5,456,711 A | 10/1995 | Hudson |
| 5,476,506 A | 12/1995 | Lunn |
| 5,487,858 A | 1/1996 | Schmitt |
| 5,496,364 A | 3/1996 | Schmitt |
| 5,505,887 A | 4/1996 | Zdrahala et al. |
| 5,509,931 A | 4/1996 | Schmitt |
| 5,522,881 A | 6/1996 | Lentz |
| 5,522,883 A | 6/1996 | Slater et al. |
| 5,527,353 A | 6/1996 | Schmitt |
| 5,545,215 A | 8/1996 | Duran |
| 5,556,426 A | 9/1996 | Popadiuk et al. |
| 5,562,725 A | 10/1996 | Schmitt et al. |
| 5,575,816 A | 11/1996 | Rudnick et al. |
| 5,607,478 A | 3/1997 | Lentz et al. |
| 5,611,127 A | 3/1997 | Ceriani et al. |
| 5,628,786 A | 5/1997 | Banas et al. |
| 5,647,848 A | 7/1997 | Jorgensen |
| 5,653,746 A | 8/1997 | Schmitt |
| 5,662,675 A | 9/1997 | Stockert et al. |
| 5,665,114 A | 9/1997 | Weadock et al. |
| 5,676,696 A | 10/1997 | Marcade |
| 5,681,322 A | 10/1997 | Hartigan, Jr. |
| 5,683,449 A | 11/1997 | Marcade |
| 5,697,969 A | 12/1997 | Schmitt et al. |
| 5,697,970 A | 12/1997 | Schmitt et al. |
| 5,702,754 A | 12/1997 | Zhong |
| 5,728,751 A | 3/1998 | Patnaik |
| 5,732,572 A | 3/1998 | Litton |
| 5,741,332 A | 4/1998 | Schmitt |
| 5,741,881 A | 4/1998 | Patnaik |
| 5,756,144 A | 5/1998 | Wolff et al. |
| 5,769,884 A | 6/1998 | Solovay |
| 5,772,864 A | 6/1998 | Moller et al. |
| 5,800,510 A | 9/1998 | Schmitt |
| 5,800,512 A | 9/1998 | Lentz et al. |
| 5,800,514 A | 9/1998 | Nunez et al. |
| 5,824,034 A | 10/1998 | Schmitt et al. |
| 5,824,047 A | 10/1998 | Moreland |
| 5,843,158 A | 12/1998 | Lenker et al. |
| 5,843,166 A | 12/1998 | Lentz et al. |
| 5,851,228 A | 12/1998 | Pinheiro |
| 5,851,229 A | 12/1998 | Lentz et al. |
| 5,851,230 A | 12/1998 | Weadock et al. |
| 5,861,026 A | 1/1999 | Harris et al. |
| 5,874,032 A | 2/1999 | Zdrahala et al. |
| 5,877,263 A | 3/1999 | Patnaik et al. |
| 5,891,195 A | 4/1999 | Klostermeyer et al. |
| 5,904,714 A | 5/1999 | Nunez et al. |
| 5,906,639 A | 5/1999 | Rudnick et al. |
| 5,910,168 A | 6/1999 | Myers et al. |
| 5,911,753 A | 6/1999 | Schmitt |
| 5,913,894 A | 6/1999 | Schmitt |
| 6,039,183 A | 3/2000 | Rudnick et al. |
| 6,039,755 A | 3/2000 | Edwin et al. |
| 6,042,592 A | 3/2000 | Schmitt |
| 6,048,620 A | 4/2000 | Zhong |
| 6,053,938 A | 4/2000 | Goldmann et al. |
| 6,059,738 A | 5/2000 | Stoltze et al. |
| 6,080,198 A | 6/2000 | Lentz et al. |
| 6,086,968 A | 7/2000 | Horovitz |
| 6,090,137 A | 7/2000 | Schmitt |
| 6,096,525 A | 8/2000 | Patnaik |
| 6,099,557 A | 8/2000 | Schmitt |
| 6,136,022 A | 10/2000 | Nunez et al. |
| 6,148,865 A | 11/2000 | Head |
| 6,162,247 A | 12/2000 | Weadock et al. |
| 6,176,875 B1 | 1/2001 | Lenker et al. |
| 6,177,609 B1 | 1/2001 | Castro et al. |
| 6,187,013 B1 | 2/2001 | Stoltze et al. |
| 6,187,033 B1 | 2/2001 | Schmitt et al. |
| 6,193,754 B1 | 2/2001 | Seedhom |
| 6,237,644 B1 | 5/2001 | Hay et al. |
| 6,250,193 B1 | 6/2001 | Head |
| 6,309,343 B1 | 10/2001 | Lentz et al. |
| 6,342,070 B1 | 1/2002 | Nguyen-Thien-Nhon |
| 6,347,632 B1 | 2/2002 | Eberhardt et al. |
| 6,352,554 B2 | 3/2002 | De Paulis |
| 6,454,796 B1 | 9/2002 | Barkman et al. |
| 6,461,382 B1 | 10/2002 | Cao |
| 6,478,817 B2 | 11/2002 | Schmitt et al. |
| 6,482,228 B1 | 11/2002 | Norred |
| 6,488,705 B2 | 12/2002 | Schmitt et al. |
| 6,494,907 B1 | 12/2002 | Bulver |
| 6,520,986 B2 | 2/2003 | Martin et al. |
| 6,540,773 B2 | 4/2003 | Dong |
| 6,544,285 B1 | 4/2003 | Thubrikar et al. |
| 6,547,820 B1 | 4/2003 | Staudenmeier |
| 6,554,855 B1 | 4/2003 | Dong |
| 6,562,069 B2 | 5/2003 | Cai et al. |
| 6,589,468 B1 | 7/2003 | Schmitt |
| 6,592,615 B1 | 7/2003 | Marcade et al. |
| 6,596,023 B1 | 7/2003 | Nuñez et al. |
| 6,613,072 B2 | 9/2003 | Lau et al. |
| 6,626,938 B1 | 9/2003 | Butaric et al. |
| 6,648,900 B2 | 11/2003 | Fleischman et al. |
| 6,652,574 B1 | 11/2003 | Jayaraman |
| 6,663,667 B2 | 12/2003 | Dehdashtian et al. |
| 6,709,440 B2 | 3/2004 | Callol et al. |
| 6,713,568 B1 | 3/2004 | Patnaik et al. |
| 6,733,525 B2 | 5/2004 | Yang et al. |
| 6,745,600 B2 | 6/2004 | Weiqing et al. |
| 6,746,458 B1 | 6/2004 | Cloud |
| 6,746,480 B2 | 6/2004 | Scholz et al. |
| 6,749,628 B1 | 6/2004 | Callol et al. |
| 6,783,554 B2 | 8/2004 | Amara et al. |
| 6,783,556 B1 | 8/2004 | Gabbay |
| 6,803,069 B2 | 10/2004 | Patnaik et al. |
| 6,821,294 B2 | 11/2004 | Nuñez et al. |
| 6,840,958 B2 | 1/2005 | Nuñez et al. |
| 6,875,230 B1 | 4/2005 | Morita et al. |
| 6,883,522 B2 | 4/2005 | Spence et al. |
| 6,887,268 B2 | 5/2005 | Butaric et al. |
| 6,893,457 B2 | 5/2005 | Dong |
| 6,939,372 B2 | 9/2005 | Dong |
| 6,953,332 B1 | 10/2005 | Kurk et al. |

| | | |
|---|---|---|
| 6,994,724 B2 | 2/2006 | Schmitt |
| 7,018,404 B2 | 3/2006 | Holmberg et al. |
| 7,044,961 B2 | 5/2006 | Lentz et al. |
| 7,160,323 B2 | 1/2007 | Pulnev et al. |
| 7,169,189 B2 | 1/2007 | Bjarnason et al. |
| 7,198,638 B2 | 4/2007 | Dong |
| 7,309,461 B2 | 12/2007 | Kujawski et al. |
| 7,314,483 B2 | 1/2008 | Landau et al. |
| 7,419,502 B2 | 9/2008 | Pulnev et al. |
| 7,431,733 B2 | 10/2008 | Knight |
| 7,465,315 B2 | 12/2008 | Morris et al. |
| 7,465,316 B2 | 12/2008 | Kujawski |
| 7,491,231 B2 | 2/2009 | Nazzaro et al. |
| 7,530,996 B2 | 5/2009 | Bentele et al. |
| 7,550,006 B2 | 6/2009 | Nuñez et al. |
| 7,618,447 B2 | 11/2009 | Case et al. |
| 7,641,687 B2 | 1/2010 | Chinn et al. |
| 7,682,381 B2 | 3/2010 | Rakos et al. |
| 7,686,844 B2 | 3/2010 | Case et al. |
| 7,717,952 B2 | 5/2010 | Case et al. |
| 7,727,271 B2 | 6/2010 | Kujawski et al. |
| 7,758,633 B2 | 7/2010 | Nazzaro |
| 7,780,720 B2 | 8/2010 | Goicoechea et al. |
| 7,806,920 B2 | 10/2010 | Duran |
| 7,833,263 B2 | 11/2010 | Thistle |
| 7,842,098 B2 | 11/2010 | Rioux et al. |
| 7,857,845 B2 | 12/2010 | Stacchino et al. |
| 7,862,609 B2 | 1/2011 | Butaric et al. |
| 7,879,085 B2 | 2/2011 | Sowinski et al. |
| 7,901,449 B2 | 3/2011 | Goicoechea et al. |
| 2001/0049553 A1 | 12/2001 | De Paulis |
| 2002/0035168 A1 | 3/2002 | Loomis et al. |
| 2002/0040247 A1 | 4/2002 | Castro et al. |
| 2002/0058991 A1 | 5/2002 | Schmitt |
| 2002/0107561 A1 | 8/2002 | Pinheiro |
| 2003/0078650 A1 | 4/2003 | Nunez et al. |
| 2003/0109919 A1 | 6/2003 | Gantt et al. |
| 2003/0130728 A1 | 7/2003 | Nunez et al. |
| 2003/0163140 A1 | 8/2003 | Stoltze et al. |
| 2003/0196717 A1* | 10/2003 | Nunez et al. ............ 139/1 R |
| 2003/0199992 A1 | 10/2003 | Schmitt et al. |
| 2004/0019375 A1 | 1/2004 | Casey et al. |
| 2004/0093065 A1 | 5/2004 | Yachia et al. |
| 2005/0070994 A1 | 3/2005 | Sievers et al. |
| 2005/0137677 A1 | 6/2005 | Rush |
| 2005/0228487 A1 | 10/2005 | Kujawski |
| 2005/0228489 A1 | 10/2005 | Kujawski |
| 2006/0178723 A1 | 8/2006 | Lentz |
| 2008/0177379 A1 | 7/2008 | Du |
| 2008/0275540 A1 | 11/2008 | Wen |
| 2009/0177271 A1 | 7/2009 | Fabiani |
| 2009/0281614 A1 | 11/2009 | Goldmann et al. |
| 2010/0063576 A1 | 3/2010 | Schaeffer et al. |
| 2010/0094390 A1 | 4/2010 | Goldmann et al. |
| 2012/0165918 A1 | 6/2012 | Du |

FOREIGN PATENT DOCUMENTS

| | | |
|---|---|---|
| DE | 101 62 821 A1 | 6/2003 |
| DE | 102 42 154 A1 | 3/2004 |
| DE | 697 28 268 T2 | 1/2005 |
| DE | 102006062360 A1 | 6/2008 |
| DE | 102007013428 A1 | 9/2008 |
| DE | 202007018508 U1 | 9/2008 |
| EP | 306690 A2 | 3/1989 |
| EP | 692225 A2 | 1/1996 |
| EP | 692264 A2 | 1/1996 |
| EP | 0955019 A2 | 11/1999 |
| EP | 1287790 A2 | 3/2003 |
| EP | 1340474 A2 | 9/2003 |
| EP | 0910310 B1 | 3/2004 |
| EP | 1935375 A1 | 6/2008 |
| EP | 2008615 A2 | 12/2008 |
| EP | 1935375 B1 | 3/2010 |
| ES | 2342431 T3 | 7/2010 |
| GB | 1173811 A | 12/1969 |
| GB | 1299963 A | 12/1972 |
| GB | 2070088 A | 9/1981 |
| JP | 03045743 A | 2/1991 |
| JP | 2010512867 A | 4/2010 |
| WO | 9509585 A1 | 4/1995 |
| WO | 9940875 A1 | 8/1999 |
| WO | 01/52776 A1 | 7/2001 |
| WO | 0224119 A1 | 3/2002 |
| WO | 02102277 A2 | 12/2002 |
| WO | 2004021925 A2 | 3/2004 |
| WO | 2005067660 A2 | 7/2005 |
| WO | 2005099624 A1 | 10/2005 |
| WO | 2008/083767 A1 | 7/2008 |
| WO | 2008083767 A1 | 7/2008 |

OTHER PUBLICATIONS (Material From Opposition to EP 1 935 375 B2) Anderson, K. et al. "Developing Seamless Shaped Woven Medical Products," Journal of Medical Engineering & Technology, May/Jun. 2004, vol. 28, No. 3, pp. 110-116.

(Material From Opposition to EP 1 935 375 B2) Anderson, K. "Seamless Textiles with Inherent Shape," North Caroline State University, Jul. 2005, Dissertation, Abstract only (3 pages).

Written Search Report and Opinion for European Patent Application No. 07024710.1 (EP 1 935 375), published Mar. 18, 2008, including partial English machine translation.

(Material From Opposition to EP 1 935 375 B2)—Notice of Opposition to European Patent Application No. 07024710.1 (EP 1 935 375)—Statement of Facts and Arguments from Opponent, Sep. 2012.

(Material From Opposition to EP 1 935 375 B2) Cross, Will, Email dated Sep. 19, 2011.

(Material From Opposition to EP 1 935 375 B2)—Notice of Opposition to European Patent EP1935375 published by EPO (23 pages)—Dated Dec. 10, 2010.

(Material From Opposition to EP 1 935 375 B2)—Submission of materials for opposition by opponent, Nov. 25, 2011 (2 pages).

(Material From Opposition to EP 1 935 375 B2) King, Dr. Martin W.—Letter to Tim Ashton, Nov. 2011.

Listing of items on the European Patent Register for EP1935375 indicating documents associated with the European Patent EP1935375. Remove dates, Sep. 2012.

(Material From Opposition to EP 1 935 375 B2—Abstract (one page) of Anderson Paper, Jul. 2005.

(Material From Opposition to EP 1 935 375 B2—Anderson Statement, Dec. 2010.

(Material From Opposition to EP 1 935 375 B2)—EPO communication dated Dec. 1, 2011 (1 page).

(Material From Opposition to EP 1 935 375 B2)—Reply from the opponent to submission of proprietor dated Nov. 25, 2011 (9 pages).

(Material From Opposition to EP 1 935 375 B2)—Reply of the patent proprietor to the notice(s) of opposition dated Jul. 19, 2011 (English translation not available) (24 pages).

(Material From Opposition to EP 1 935 375 B2)—Materials Cited in Opposition Request—(5 pages) (dated Dec. 10, 2010).

U.S. Appl. No. 12/387,201, filed Apr. 29, 2009, inventor is George Du.

U.S. Appl. No. 11/655,438, filed Jan. 19, 2007, inventor is George Du.

Hughes, G. Chad, Reimplantation Technique (David Operation) for Multiple Sinus of Valsalva Aneurysms, Ann Thorac Surg 2006; 82:e14-16.

Thubrikar, Mano J., Stress Sharing Between the Sinus and Leaflets of Canine Aortic Valve, Ann Thorac Surg, 1986;42:434-440.

Bentall, Hugh, A Technique for Complete Replacement of the Ascending Aorta, Thorax (1968) 23, 338-339.

Kunzelman, Karyn S., Surgery for Acquired Disease: Aortic root and valve relationships: Impact on Surgical Repair, J. Thorac Cardiovasc. Surg 1994;107:162-170.

Bellhouse, B.J., Velocity and Pressure Distributions in the Aortic Valve, J. Fluid Mech. (1969), vol. 37, part 3, pp. 587-600, Great Britain.

Svensson, Lars G., Composite Valve Graft Replacement of the Proximal Aorta: Comparison of Techniques in 348 Patients, Ann Thorac Surg 1992;54:427-439, 1992.

Cabrol, C., Complete Replacement of the Ascending Aorta with Reimplantation of the Coronary Arteries, J. Thorac Cardiovasc Surg. 81:309-315, 1981.

David, T. E., Feindel, C. M., Bos J.: Repair of the aortic valve in patients with aortic insufficiency and aortic root aneurysm. J Thorac Cardiovasc Surg 1995; 109(2):345-51.

David, T. E., Feindel, C. M., An Aortic Valve-Sparing Operation for Patients with Aortic Incompetence and Aneurysm of the Ascending Aorta, The Journal of Thoracic and Cardiovascular Surgery, vol. 103, 617-621, 1992.

David, Tirone E., Feindel, Christopher M., Surgery for Acquired Heart Disease, Repair of the aortic valve in patients with aortic insufficiency and aortic root aneurysm, J. Thorac Cardiovac Surg 1995;109:345-352, Canada.

Sarsam, M.A., Yacoub, M, Remodeling of the aortic valve annulus, The Journal of Thoracic and Cardiovascular Surgery, vol. 105, 435-438, 1993.

Bellhouse B. J.: The fluid mechanics of the aortic valve. In: Ionescu M. L., Ross D. N., Woller G. H., eds. Biological tissue heart replacement. London: Butterworth-Heinemann, 1972:32-8.

Richardt, Dorreen, A New Sinus Prosthesis for Aortic Valve-Sparing Surgery Maintaining the Shape of the Root at Systemic Pressure, Ann Thorac Surg, 2010; 89:943-946.

US 7,905,914, 03/2011, Goicoechea et al. (withdrawn).

* cited by examiner

SINGLE CONTINUOUS PIECE PROSTHETIC TUBULAR AORTIC CONDUIT AND METHOD FOR MANUFACTURING THE SAME

RELATED APPLICATIONS

The present application is a continuation of U.S. application Ser. No. 12/387,201 filed Apr. 29, 2009, abandoned, which is a continuation of U.S. application Ser. No. 12/590,906 filed Nov. 16, 2009, abandoned, which is a continuation of U.S. application Ser. No. 11/655,438 filed Jan. 19, 2007, abandoned.

BACKGROUND OF THE INVENTION

The normal internal human aortic root conduit is provided with a sinus portion which has three sinuses (bulges) which surround the aortic valve. These sinuses are called sinuses of Valsalva and are arranged so that the cross-section of the sinus portion has a generally trefoil shape. The diameter and orifice area of the root are greater at the level of the sinus, decrease slightly at the base, but significantly decrease (by 20%) at the level of the sinotubular junction (where the sinus portion connects to the ascending portion of the aorta which supports the two iliac arteries).

The sinotubular junction or sinus ridge and the sinuses of Valsalva are known to be crucial for the normal function of the aortic valve. The sinus ridge is important in causing initial fluid flow eddies inside the sinuses of Valsalva (see Bellhouse B J: Velocity and pressure distributions in the aortic valve. J Fluid Mech 1969; 37(3): 587-600 and Bellhouse B. J.: The fluid mechanics of the aortic valve. In: Ionescu M. L., Ross D. N., Woller G. H., eds. Biological tissue heart replacement. London: Butterworth-Heinemann, 1972: 32-8). During systole, the aortic valve opens and the eddy currents created prevent the leaflets of the aortic valve from impacting on the aortic wall. Then, at the end of systole, the eddy currents inside the sinuses cause the leaflets of the aortic valve to become almost closed. Furthermore, the sinus curvature is very important in sharing stress with the leaflet. It has been demonstrated that during diastole the sinus walls move outwardly (increasing its circumferential curvature by 16%) taking up part of the load placed on the leaflet. Further it is known (see (Thubrikar M. J., Nolan S. P., Aouad J., Deck D.; Stress sharing between the sinus and leaflets of canine aortic valve. Ann Thorac Surg 1986; 42(4):434-40)) that the longitudinal length of the sinus changes very little or does not change at all during the cardiac cycle. In other words during the functioning of the aortic valve the sinus moves up and down as a whole without changing its length.

The standard surgical approach in patients with ascending aortic aneurysm or dissection involving the aortic root and associated with aortic valve disease is the replacement of the aortic valve and ascending aorta by means of a composite and valved graft onto which are reattached the two coronary arteries as originally described by Bentall and de Bono in their classical paper (Bentall H. H., De Bono A.: A technique for complete replacement of the ascending aorta, Thorax 1968; 23: 338-9). The "open" (Carrel button) method of coronary reimplantation was later recommended to decrease the tension on the coronary ostia while minimizing the risk of late false aneurysm formation. This "Carrel button" method has already reduced the incidence of pseudoaneurysm formation mainly through the reduction of the tension on the ostial anastomoses (see Svensson L. G.; Crawford E. S.; Hess K. R.; Coselli J. S.; Safi H. J.; Composite valve graft replacement of the proximal aorta: comparison of techniques in 348 patients. Ann Thorac Surg 1992, 54(3) 427-370). A modification of the standard technique was also introduced by Cabrol et al (Cabrol C, Pavie A, Gandjbakhch I. et al: Complete replacement of the ascending aorta with reimplantation of the coronary arteries. New Surgical approach, J Thorac Cardiovasc Surg 1981: 81; 309-15) for those cases of difficult presentation (low lying coronary ostia, calcified coronary ostia, tissue fibrosis in redo cases) where the coronary ostia are reattached to the aortic conduit by interposition of a small conduit.

If the aortic valve leaflets are normal, a valve-sparing aortic root remodeling procedure which keeps the natural patient valve on site is a reasonable alternative in certain individuals. David and Feindel (David T. E., Feindel C. M.: An aortic valve-sparing operation for patients with aortic incompetence and aneurysm of the ascending aorta, J Thorac Cardiovasc Surg 1992; 1 03(4): 617-21) described a surgical technique where the dilated aortic root is replaced with a tube made of DACRON fibers and the native aortic valve is integrated within the graft. This method is generally known as the "Tirone David Type I aortic valve sparing procedure". However, the lack of sinuses in a straight tube graft was found to negatively influence proper valve function, with the consequent risk of decreasing valve longevity (Kunzelman K. S., Grande K. J., David T. E., Cochran R. P., Verrier E. D.: Aortic root and valve relationships. Impact on surgical repair J Thorac Cardiovascular Surg 1995; 109(2): 345-51).

Thus in the Tirone David Type I technique for valve sparing operations, the use of a straight tube without a sinus component raises several problems: opening and closing of the native valve is not optimal. For example, upon valve opening, the leaflets might impact on the graft and be potentially damaged. The absence or delay in eddy current formation might alter valve closure causing some regurgitation. Furthermore, the diastolic stress is borne only by the leaflet and is not shared with the sinuses causing a potential decrease in leaflet longevity.

An optimal design for root replacement should therefore incorporate sinuses and a sinotubular junction and further refinement of the technique consisted of trimming one end of the aortic tube graft to produce three separate extensions designed to replace the three sinuses. The reshaped DACRON tube was then sutured to the aortic valve remnants (see David T. E., Feindel C. M., Bos J.: Repair of the aortic valve in patients with aortic insufficiency and aortic root aneurysm. J Thorac Cardiovasc Surg 1995; 109(2):345-51) to obtain a final configuration resembling more closely the native aortic root. A similar technique was also described by Yacoub el al (Saram M. A., Yacoub M.: Remodeling of the aortic valve annulus. J Thorac Cardiovasc Surg 1993; 105(3): 435-8) several years previously.

In U.S. Pat. No. 5,139,515 it was proposed to provide an aortic graft having a lower portions provided with "bulges" apparently mimicking the sinuses of Valsalva. However no method to produce such a conduit for use in aortic surgery is described in the patent. U.S. Pat. No. 5,139,515 described a conduit having an "annular wall of a crimped material similar to that of conventional prosthesis". No indication is actually given of how to obtain the "annually-spaced radially outward bulges" mimicking the sinuses. Moreover the drawings clearly show that the conduit, including the sinus portion, is provided along its whole length with corrugations which lie perpendicularly to the longitudinal axis of the prosethesis, and which impart longitudinal elasticity to the whole of the conduit. Upon implantation, the graft cannot expand radially outwardly, but has the potential to move and extend in the longitudinal direction of the longitudinal axis of the prosthesis.

Or as disclosed in U.S. Pat. No. 6,352,554, a conduit may comprise two distinct tubular portions having a common axis. The first upper portion is made form a standard aortic conduit and is provided with circumferentially extending corrugations successively provided along the axis of the tubular first portion. The second lower portion, or skirt portion is a tube which can be made of the same material as the first portion (that is, any suitable biocompatible material, but preferably DACRON or PTFE) but which is provided with longitudinally extending pleats or corrugations. Each of these corrugations extends in the general direction of the longitudinal axis of the prosthesis and is positioned substantially perpendicularly to the circumferential corrugations of the first portion.

The proximal end of skirt portion 14 is attached to the distal end portion of the first portion 12 so the two connected portions have essentially the same lumen and form the tubular conduit 10.

Notwithstanding the above it is still preferred to have a single conduit, that can limit leakage, and avoid the need to connect two or more tubes to form the conduit.

Therefore there is still a need for an effective prosthetic conduit to replace the aortic root while providing all the advantages of the natural sinuses of Valsalva.

SUMMARY OF THE INVENTION

It is therefore one of the objects of the invention to provide a prosthetic aortic conduit which overcomes the drawbacks mentioned above and which upon implantation has the ability to expand radially outwardly whilst maintaining a degree of flexibility in the longitudinal direction.

It is another object of the invention to provide a conduit which is specifically designed to closely mimic the sinuses of Valsalva.

A first object of the invention is a prosthetic aortic conduit for replacing a root portion of an aorta which comprises a first tubular portion and a second tubular portion connected together along a substantially common axis. The second tubular portion does not substantially deform in a longitudinal direction and has an expansion portion in a lateral direction.

It is preferred that the prosthetic aortic conduit be made of polyester or PTFE material or any other material capable of being woven.

It is further preferred that another portion of the conduit of the invention comprises annular corrugations successively provided along the longitudinal axis of said conduit.

It is further preferred that the first and second portions of the conduit be made of a single woven tube along a common axis.

It is further preferred that the conduit is provided with a third tubular portion which is part of the continuous conduit provided with resilient means which allows expansion of said third portion in a longitudinal direction.

Where a third portion of the conduit is required or used the weave will simply be continued from the second portion of the conduit.

DESCRIPTION OF PREFERRED EMBODIMENTS OF THE INVENTION

Figure 1:
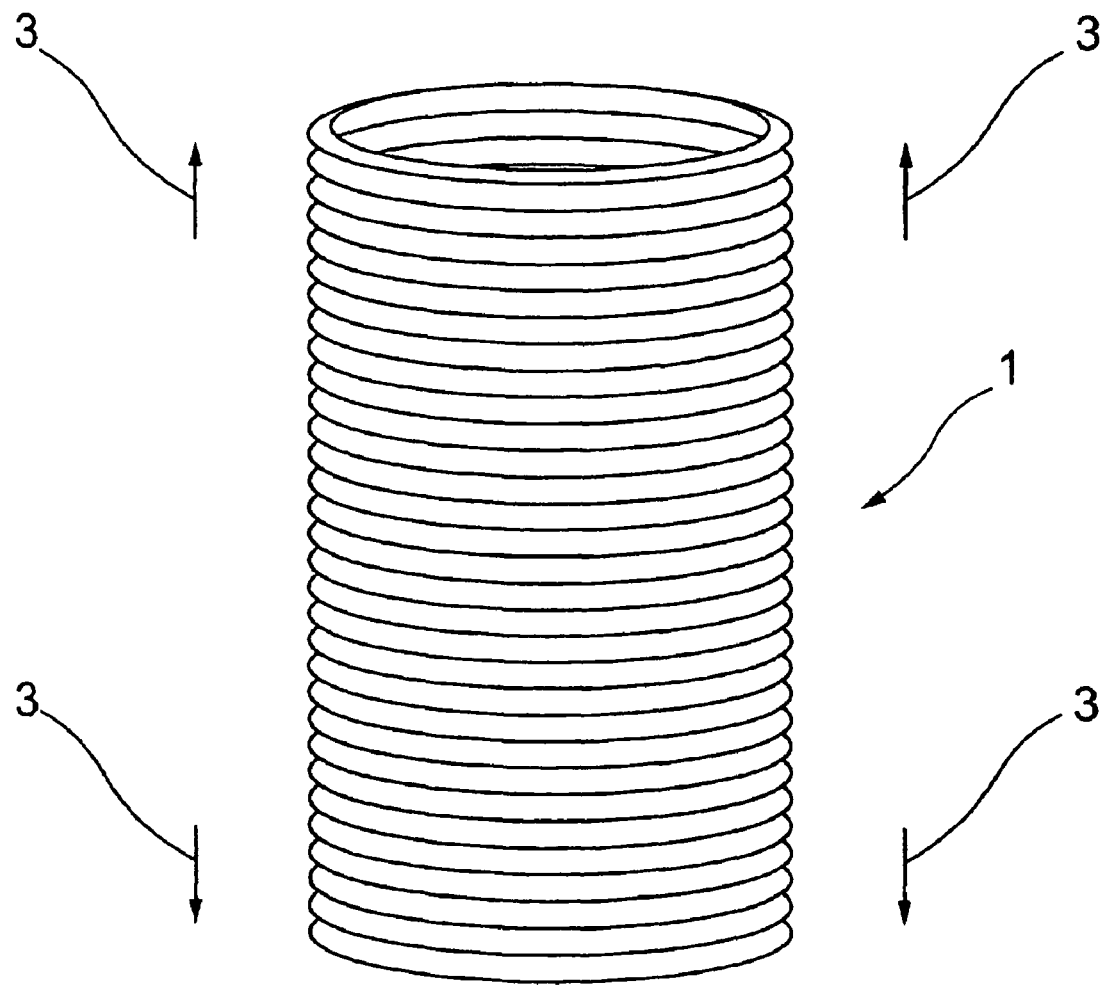
FIG. 1 is a representation of a known aortic conduit, showing corrugations which lie traverse to the longitudinal axis of the prosthesis.

FIG. 1 shows a standard aortic conduit 1 of the type currently used in aortic surgery. This conduit is made of DACRON but any suitable biocompatible material such as polytetrafluoroethylene (PTFE) could be used. This standard aortic conduit 1 includes circumferentially extending pleats so that the corrugations lie perpendicular to the longitudinal axis of the prosthesis. These corrugations provide a degree of expansion in the longitudinal direction (indicated by the black arrows 3 in FIG. 1) and the conduit 1 can therefore significantly increase its length.

Figure 2:
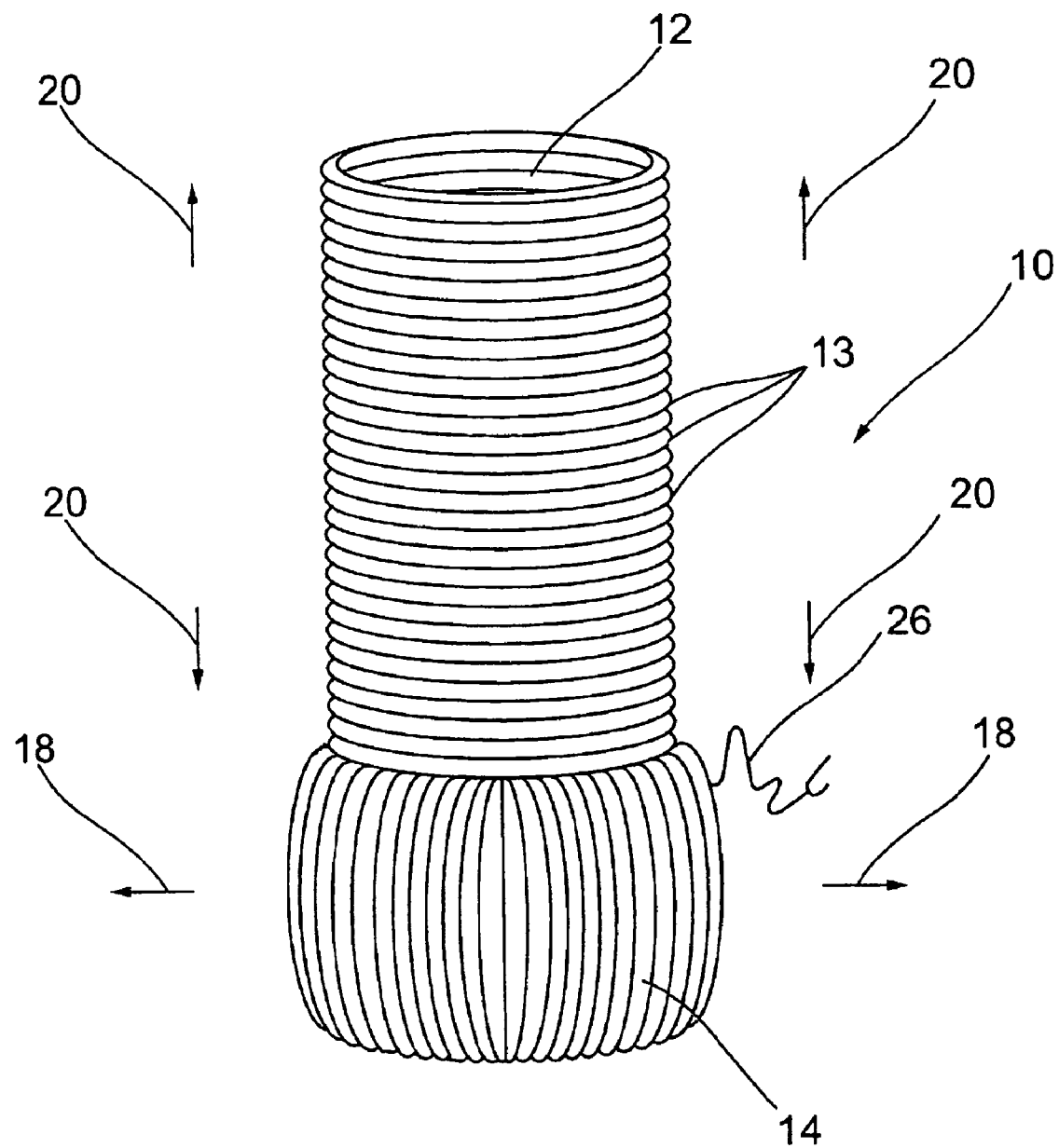
FIG. 2 is a representation of another known aortic conduit.

FIG. 2 shows a preferred embodiment of the conduit of the invention. The conduit 10 comprises two distinct tubular portions having a common axis. The first upper portion 12 is made from a standard aortic conduit similar to the one shown in FIG. 1 and is provided with circumferentially extending corrugations 13 successively provided along the axis of the tubular first portion 12. The second lower portion, or skirt portion, 14 is a tube which can be made of the same material as the first portion (that is, any suitable biocompatible material) but which has longitudinally extending pleats or corrugations 16.

The proximal end of skirt portion 14 is attached to the distal end portion of the first portion 12 so the two connected portions have essentially the same lumen and form the tubular conduit 10.

Figure 3:
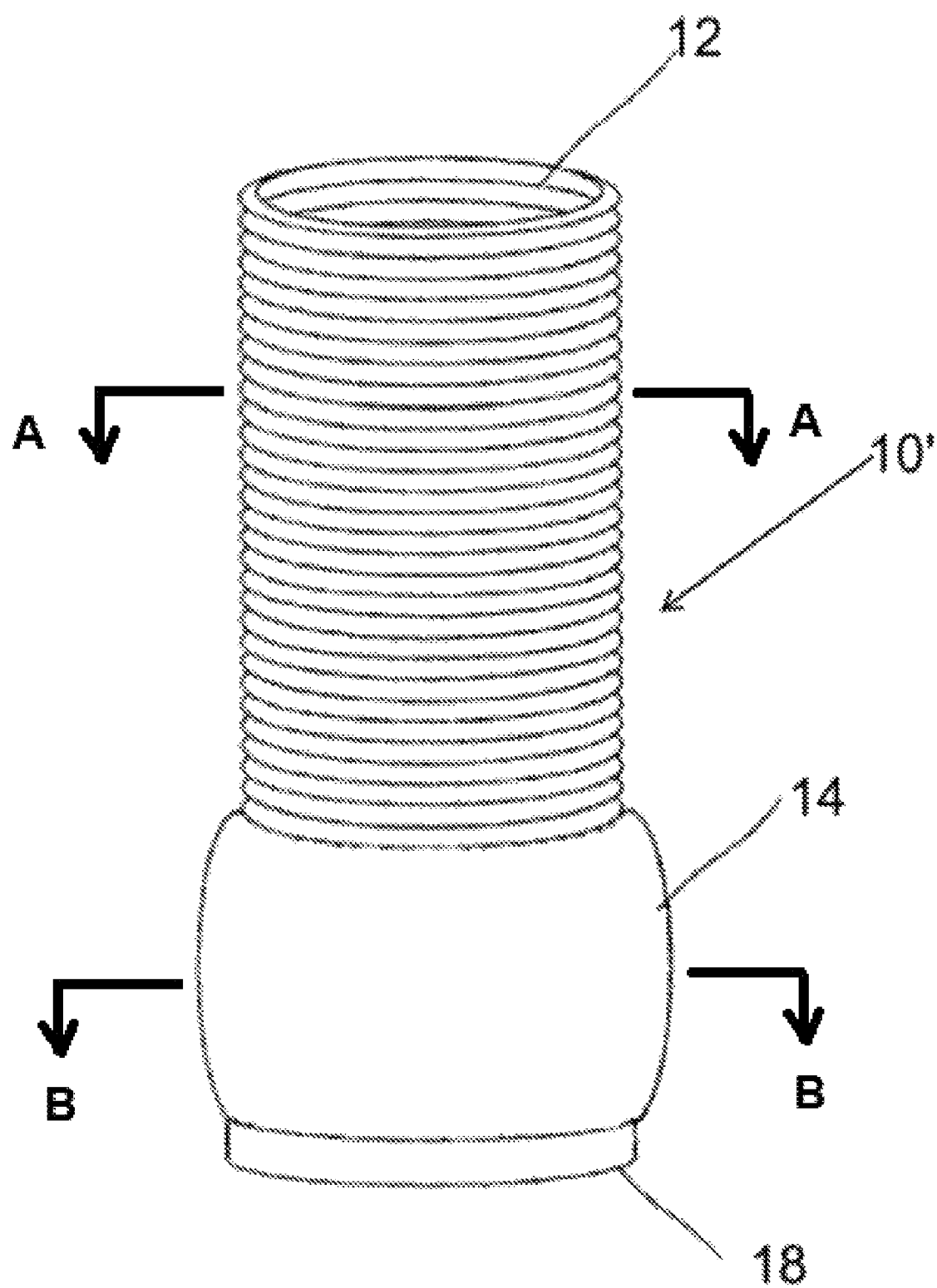
FIG. 3 is a prosthetic aortic conduit according to the first preferred embodiment of the invention.

As shown in FIG. 3, which is one embodiment of the preferred invention, the first portion 12 and the skirt portion 14 with their respective corrugations 13 orientated at an angle of about 90 degrees will act, upon implantation, as a "sinotubular junction" witch it internal diameter will be significantly less than the internal diameter of its lower part, namely second portion 14. Once the prosthetic aortic conduit 10' is in place the internal diameter of the skirt portion 14 will vary during the cardiac cycle (systole/diastole) as in the natural aortic root. Thus, the skirt portion 14, when filled with blood under pressure, will stretch in the direction traverse to the longitudinal axis of the prostheses (the lateral direction) mimicking the "sinuses of Valsalva". However, the skirt portion 14 does not, however, allow that section of the prosthesis to increase in length and has a collar 18 for attachment purposes.

Thus the skirt portion 14 can move and expand in a lateral direction only, while the first portion 12 of conduit 10' can extend in the longitudinal direction only. The resiliency of the skirt portion 14 in the general lateral direction is shown in FIG. 2 by the arrows 18 and the expansion of the first portion 12 in the general longitudinal direction is shown by the arrows 2.

Figure 4:
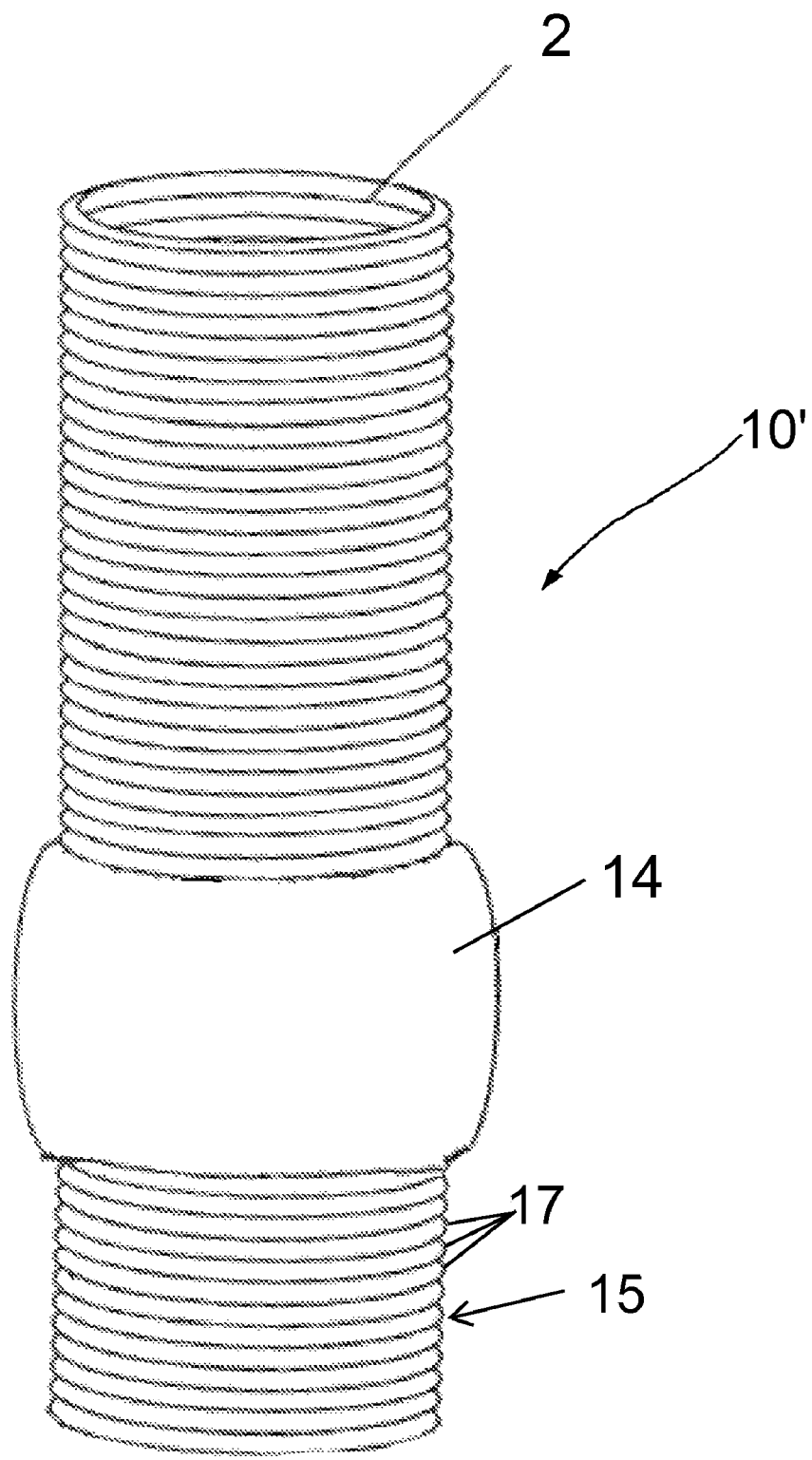
FIG. 4 is a prosthetic aortic conduit according to a second preferred embodiment of the invention.

In an alternative embodiment shown in FIG. 4, a third tubular portion 15 is attached to the distal end of the skirt portion 14. The third tubular portion 15 is aligned on the same common axis as the first and second portions 12 and 14. The third portion 15 is advantageously made of any length that is desired. It is typically made of DACRON or similar material or any material that may be weaved and is provided with circumferentially extending corrugations or pleats 17 in the same manner as the first portion 12.

Preferred Method of Manufacture of a Conduit According to the Invention

Figure 5:
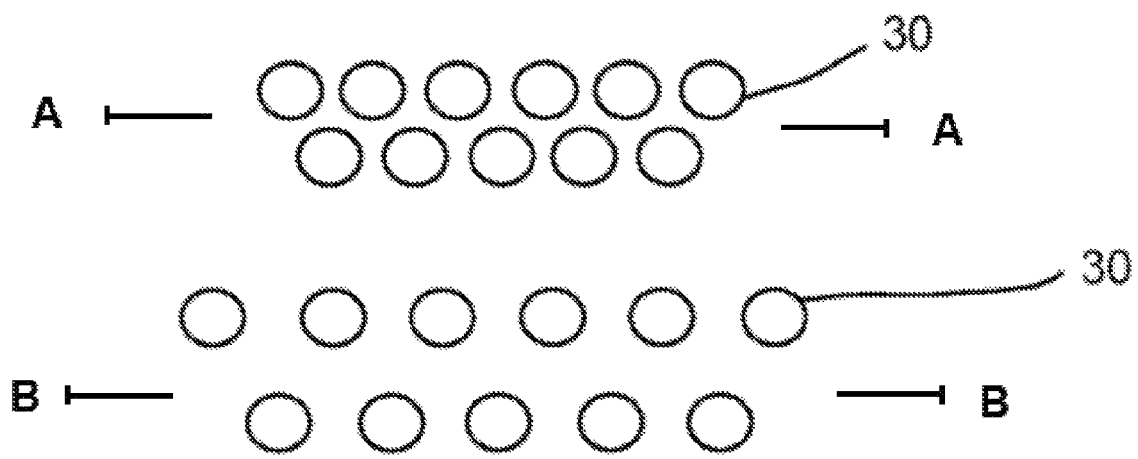
FIG. 5 is a cross-sectional view of the individual rows of yarn forming the weave of the aortic conduit of FIG. 3 in a flattened configuration, showing a first portion A where the individual rows of weave are close and a second portion B where the individual rows of weave are further apart.

The conduit 10' may be manufactured as shown in FIG. 5, by changing the tightness of each row of the individual weave material 30 to create the desired diameter of the conduit 10'.

The device and method of manufacture according to the present invention have been described in the foregoing specification. However, the invention which is intended to be protected is not to be construed as limited to the particular embodiments disclosed. Further, the embodiments described herein are to be regarded as illustrative rather that restrictive. Variations, changes and equivalents may be made by others without departing from the spirit of the present invention. Accordingly, it is expressly intended that all such variation, changes and equivalents which fall within the spirit and scope of the present invention as defined in the claims, be embraced thereby.

I claim:

1. An aortic prosthetic comprising:
a conduit having a first portion, a skirt portion, and a third portion, all continuously woven together, wherein the skirt portion has a larger diameter than the first portion or the third portion, and a tightness of rows of yarn in the skirt portion is different than a tightness of rows of yarn in the first and the third portion.

2. The aortic prosthetic of claim 1, wherein the conduit is configured to mimic the sinuses of Valsalva.

3. The aortic prosthetic of claim 1, wherein the yarn is polyester, Dacron, or PTFE.

4. The aortic prosthetic of claim 1, wherein the first portion, the skirt portion, and the third portion share a common axis.

5. An aortic prosthetic comprising:
rows of yarn forming a continuously woven conduit, wherein the continuously woven conduit comprises:
a first portion comprising a first diameter; and
a skirt portion comprising a second diameter larger than the first diameter,
wherein spacing between a plurality of the rows of yarn are closer in the skirt portion than spacing between the plurality of the rows of yarn in the first portion.

6. The aortic prosthetic of claim 5, wherein the continuously woven conduit minimizes leakage of blood when blood is conducted through the continuously woven conduit under cardiac pressure.

7. The aortic prosthetic of claim 5, wherein at least one portion of the continuously woven conduit is capable of resiliently expanding to mimic sinuses of Valsalva.

8. The aortic prosthetic of claim 5, wherein the skirt portion is capable of resiliently expanding, wherein the second diameter is capable of varying when filled with blood under pressure.

9. The aortic prosthetic of claim 5, wherein one or more portions of the continuously woven conduit comprises pleats circumferentially extending around the continuously woven conduit allowing expansion of the one or more portions in a longitudinal direction of the continuously woven conduit.

10. The aortic prosthetic of claim 9, wherein the one or more portions comprises the first portion of the continuously woven conduit.

11. The aortic prosthetic of claim 10, wherein the one or more portions further comprises a third portion of the continuously woven conduit that adjoins the second portion.

12. The aortic prosthetic of claim 9, wherein the one or more portions is only expandable in a longitudinal direction with respect to the continuously woven conduit.

13. The aortic prosthetic of claim 5, wherein the skirt portion comprises longitudinally extending pleats allowing expansion of the skirt portion in a lateral direction transverse to a longitudinal axis of the continuously woven conduit.

14. The aortic prosthetic of claim 5, wherein the skirt portion is restricted from expanding in a longitudinal direction with respect to the continuously woven conduit.

15. The aortic prosthetic of claim 5, wherein the yarn is constructed from a material selected from the group consisting of: Dacron, and polytetrafluoroethylene.

16. The aortic prosthetic of claim 5, wherein the continuously woven conduit defines a lumen axially extending through the first portion and the skirt portion.

17. The aortic prosthetic of claim 5, wherein the continuously woven conduit further comprises a third portion comprising a diameter different than the second diameter.

18. The aortic prosthetic of claim 5, wherein the rows of yarn extend through the first portion and the skirt portion and said rows of yarn are closer in the skirt portion than they are in the first portion.

19. An aortic prosthetic comprising:
a first portion comprising a first diameter;
a skirt portion comprising a second diameter larger than the first diameter; and
a third portion,
wherein the first portion, the skirt portion and the third portion form a woven conduit, and wherein spacing between rows of yarn forming the skirt portion are closer than spacing between rows of yarn forming at least one of the first portion and the third portion.

20. A method of manufacturing a prosthetic aortic conduit having first and second ends, and rows of yarns of varying spacing, the method comprises the following steps:
weaving a first conduit suitable for use in heart surgery, said first conduit having a longitudinal axis;
continuing weaving of the first conduit to form a skirt conduit suitable for use in heart surgery, wherein the skirt conduit has a larger diameter than that of the first conduit, and a spacing of the rows of yarn used to weave the prosthetic aortic conduit is different in the skirt conduit than the first conduit; and
continuing the weave of the skirt conduit to form a third conduit.

21. The method of claim 20, wherein a spacing of the rows of yarn used to weave the third conduit is different than the spacing of the rows of yarn used to weave the skirt conduit.

22. The method of claim 20, wherein the skirt conduit is configured to mimic the sinuses of Valsalva.

23. The method of claim 20, wherein the yarn is polyester, Dacron, or PTFE.

24. The method of claim 20, wherein the first conduit, the skirt conduit, and the third conduit share a common axis.

* * * * *